(12) United States Patent
Reyes

(10) Patent No.: US 12,059,373 B2
(45) Date of Patent: Aug. 13, 2024

(54) FLUID DRIVEN VITRECTOMY PROBE

(71) Applicant: Alcon Inc., Fribourg (CH)

(72) Inventor: Nathaniel Reyes, Santa Ana, CA (US)

(73) Assignee: Alcon Inc., Fribourg (CH)

( * ) Notice: Subject to any disclaimer, the term of this patent is extended or adjusted under 35 U.S.C. 154(b) by 258 days.

(21) Appl. No.: 17/452,600

(22) Filed: Oct. 28, 2021

(65) Prior Publication Data
US 2022/0160544 A1 May 26, 2022

Related U.S. Application Data

(60) Provisional application No. 63/116,194, filed on Nov. 20, 2020.

(51) Int. Cl.
*A61F 9/007* (2006.01)

(52) U.S. Cl.
CPC .................. *A61F 9/00763* (2013.01)

(58) Field of Classification Search
CPC ........... A61F 9/00763; A61B 17/32002; A61B 17/3207; A61B 17/320758; A61B 2017/320028
See application file for complete search history.

(56) References Cited

U.S. PATENT DOCUMENTS

| | | | |
|---|---|---|---|
| 4,940,468 A * | 7/1990 | Petillo | A61F 9/00763 604/22 |
| 5,176,628 A | 1/1993 | Charles et al. | |
| 8,080,029 B2 | 12/2011 | Charles | |
| 8,187,293 B2 | 5/2012 | Kirchhevel | |
| 8,540,743 B2 | 9/2013 | Auld | |
| 8,888,802 B2 | 11/2014 | Underwood | |
| 9,101,442 B2 | 8/2015 | Mcdonell | |
| 9,517,161 B2 | 12/2016 | Underwood | |
| 9,655,777 B2 | 5/2017 | Gelvin | |
| 9,693,898 B2 | 7/2017 | Farley | |
| 9,974,689 B2 | 5/2018 | Mcdonell | |
| 10,111,777 B2 | 10/2018 | Gunn | |
| 10,369,046 B2 | 8/2019 | Mcdonell | |
| 10,383,766 B2 | 8/2019 | Farley | |
| 10,537,471 B2 | 1/2020 | Bourne | |
| 10,555,834 B2 | 2/2020 | Charles | |
| 10,639,197 B2 | 5/2020 | Lopez | |
| 10,893,978 B2 | 1/2021 | Sawicz | |
| 10,918,411 B2 | 2/2021 | Mcdonell | |
| 2007/0185512 A1* | 8/2007 | Kirchhevel | A61F 9/00763 606/170 |
| 2007/0185514 A1 | 8/2007 | Kirchhevel | |
| 2007/0260183 A1* | 11/2007 | Shores | A61B 17/1628 604/131 |

(Continued)

*Primary Examiner* — Ashley L Fishback
*Assistant Examiner* — Chima U Igboko
(74) *Attorney, Agent, or Firm* — PATTERSON + SHERIDAN, LLP

(57) ABSTRACT

The present disclosure generally relates to a fluid-driven vitrector for vitreo-retinal procedures. The vitrector includes a first fluid pathway containing a first fluid and a second fluid pathway containing a second fluid that are completely sealed from an external environment. Because the fluid pathways are completely sealed from an external environment, an alternative fluid that can transmit pressure waves faster than air may be utilized as the first and second fluids to drive the vitrector.

16 Claims, 5 Drawing Sheets

(56) References Cited

U.S. PATENT DOCUMENTS

| | | | |
|---|---|---|---|
| 2009/0259242 A1* | 10/2009 | Gerg | A61F 9/00736 |
| | | | 606/167 |
| 2014/0171994 A1* | 6/2014 | Lee | A61F 9/00763 |
| | | | 606/170 |
| 2016/0095615 A1* | 4/2016 | Orczy-Timko | A61B 18/1485 |
| | | | 606/171 |
| 2017/0172796 A1 | 6/2017 | Biancalana | |
| 2019/0000672 A1* | 1/2019 | McDonell | A61F 9/00763 |
| 2019/0183679 A1* | 6/2019 | Sawicz | A61B 17/00 |
| 2020/0016001 A1 | 1/2020 | Mcdonell | |

* cited by examiner

FLUID DRIVEN VITRECTOMY PROBE

PRIORITY CLAIM

This application claims the benefit of priority of U.S. Provisional Patent Application Ser. No. 63/116,194 titled "FLUID DRIVEN VITRECTOMY PROBE," filed on Nov. 20, 2020, whose inventor is Nathaniel Reyes, which is hereby incorporated by reference in its entirety as though fully and completely set forth herein.

FIELD

The present disclosure relates generally to small-gauge instrumentation for surgical procedures, and more specifically, to a fluid driven vitrectomy probe for vitreo-retinal procedures.

BACKGROUND

Vitreo-retinal procedures may include a variety of surgical procedures performed to restore, preserve, and enhance vision. Vitreo-retinal procedures may be appropriate to treat many serious conditions of the back of the eye. For example, vitreo-retinal procedures may treat conditions such as age-related macular degeneration (AMD), diabetic retinopathy and diabetic vitreous hemorrhage, macular hole, retinal detachment, epiretinal membrane, CMV retinitis, as well as other ophthalmic conditions.

The vitreous is a normally clear, gel-like substance that fills the center of the eye. It may make up approximately two-thirds of the eye's volume, giving it form and shape before birth. Certain problems affecting the back of the eye may require a vitrectomy, or surgical removal of the vitreous. For example, a vitrectomy may be performed to clear blood and debris from the eye, to remove scar tissue, or to alleviate traction on the retina. The vitreous may also be removed if it is pulling or tugging the retina from its normal position.

Removal of vitreous can involve a vitrector (also referred to as the "cutter", "vitreous cutter," or "vitrectomy probe"), that works like a tiny guillotine, with an oscillating microscopic cutter to remove the vitreous gel in a controlled fashion. In some examples, the cutter is powered by an air-driven vitrectomy machine ("surgical console") including one or more drive valves. For example, the cutter may be powered by pressurized air that is alternately directed from a pressurized air source to the cutter through the one or more drive valves and gas lines. In other examples, the cutter is powered by an electrically-driven motor.

Generally, the cutter is desired to be operated at high speed (e.g., high cut rate) in order to reduce traction during a vitrectomy procedure. When utilizing an air-driven vitrector, however, the oscillation frequency of the cutter, and thus, the cut rate of the cutter, is limited by the speed at which air pressure can be adjusted. While electrically-driven vitrectors are not limited by the same fluid mechanics, electrically-driven probes tend to be weighty, cumbersome, and costly as compared to their air-driven counterparts.

Therefore, what is needed in the art is an improved vitrectomy probe having increased actuation rates for vitreo-retinal procedures.

SUMMARY

According to certain embodiments, a surgical tool is provided. The surgical tool includes a housing, a first fluid pathway retaining a first fluid and completely sealed from an external environment, a second fluid pathway retaining a second fluid and completely sealed from an external environment, a diaphragm disposed within the housing, and a cutting member coupled to the diaphragm. The first fluid pathway includes a first chamber within the housing and having a first port, and a first channel coupled to the first port and extending from the housing. The second fluid pathway includes a second chamber within the housing and having a second port, and a second channel coupled to the first port and extending from the housing. The diaphragm separates the first chamber from the second chamber and is axially movable relative to the housing and between the first chamber and the second chamber. Alternating a flow direction of the first and second fluids through the first and second fluid pathways axially drives the diaphragm in an oscillating manner. Axial motion of the diaphragm, in turn, causes axial motion of the cutting member.

According to certain embodiments, a surgical system is provided. The surgical system includes a surgical tool, a controller, and a first actuator. The surgical tool includes a housing, a first fluid pathway retaining a first fluid and completely sealed from an external environment, a second fluid pathway retaining a second fluid and completely sealed from an external environment, a diaphragm disposed within the housing, and a cutting member coupled to the diaphragm. The first fluid pathway includes a first chamber within the housing and having a first port, and a first channel coupled to the first port and extending from the housing. The second fluid pathway includes a second chamber within the housing and having a second port, and a second channel coupled to the first port and extending from the housing. The diaphragm separates the first chamber from the second chamber and is axially movable relative to the housing and between the first chamber and the second chamber. Alternating a flow direction of the first and second fluids through the first and second fluid pathways axially drives the diaphragm in an oscillating manner. Axial motion of the diaphragm, in turn, causes axial motion of the cutting member. The controller produces an output signal representing a desired oscillation frequency of the cutting member, and the first actuator, which is in communication with the controller and at least one of the first and second pathways, is configured to receive the output signal of the controller and drive the flow direction of at least one of the first and second fluids in the first and second fluid pathways.

BRIEF DESCRIPTION OF THE DRAWINGS

So that the manner in which the above-recited features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, and may admit to other equally effective embodiments.

To facilitate understanding, identical reference numerals have been used, where possible, to designate identical elements that are common to the Figures. It is contemplated that elements and features of one embodiment may be beneficially incorporated in other embodiments without further recitation.

DETAILED DESCRIPTION

In the following description, details are set forth by way of example to facilitate an understanding of the disclosed subject matter. It should be apparent to a person of ordinary skill in the field, however, that the disclosed implementations are exemplary and not exhaustive of all possible implementations. Thus, it should be understood that reference to the described examples is not intended to limit the scope of the disclosure. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one implementation may be combined with the features, components, and/or steps described with respect to other implementations of the present disclosure.

Embodiments of the present disclosure generally relate to vitrectomy probes and vitrectomy probe systems for vitreoretinal surgical procedures. A vitrector includes a first fluid pathway containing a first fluid and a second fluid pathway containing a second fluid that are completely sealed from an external environment. The fluid pathways are partially disposed within tubes that extend proximally and externally from a housing of the vitrector and are configured to be inserted or attached to a surgical console to drive flow directions of the first and second fluids contained therein. Alternating flow directions of the fluids within the fluid pathways drives an oscillating cutting motion of the vitrector. Because the fluid pathways are completely sealed from an external environment, an alternative fluid that can transmit pressure waves faster than air may be utilized as the first and second fluids, thus facilitating faster cutting rates than conventional air-driven vitrectomy probes and reducing traction.

As used herein, the term "about" may refer to a +/−10% variation from the nominal value. It is to be understood that such a variation can be included in any value provided herein.

Figure 1:
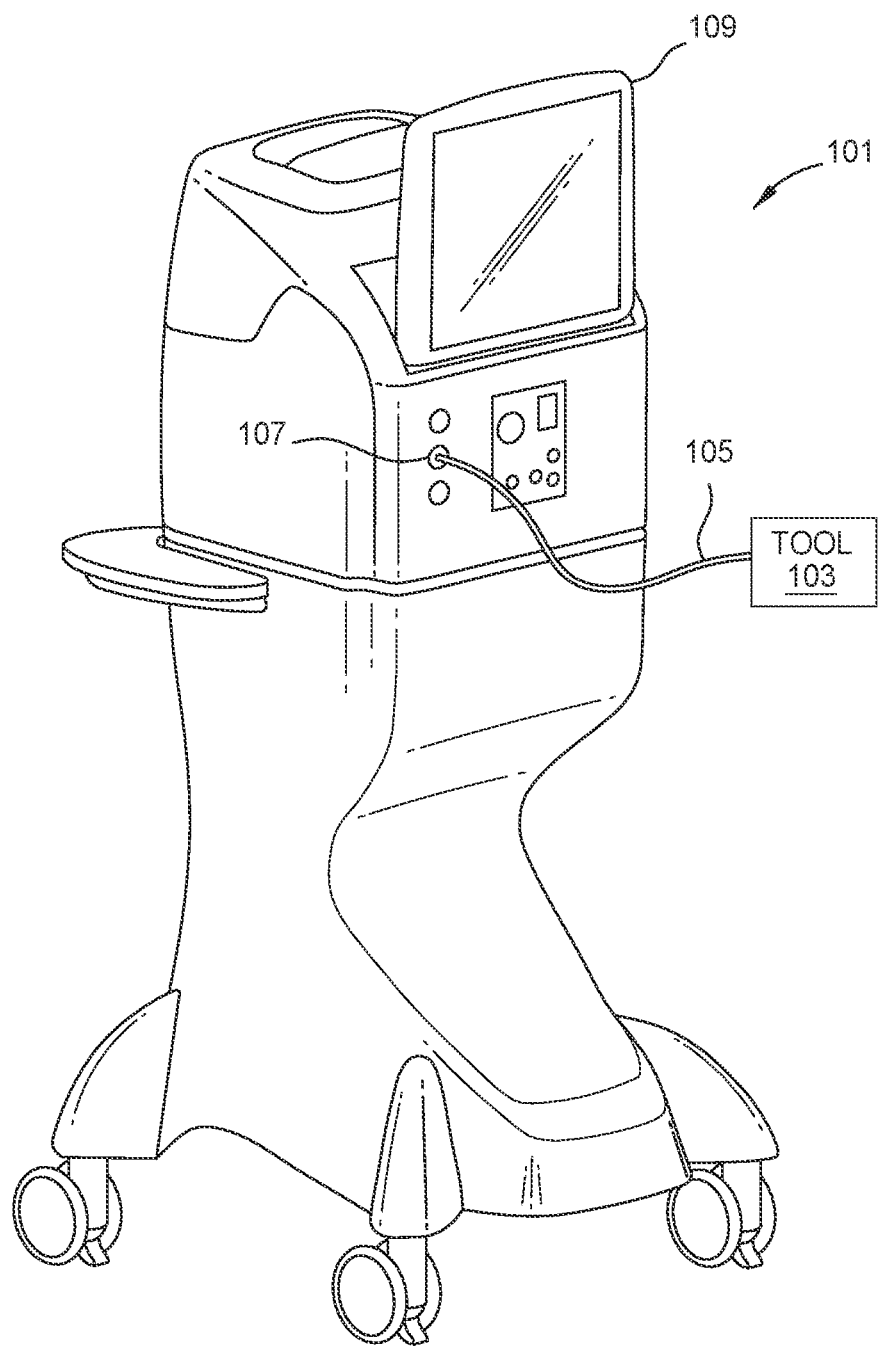
FIG. 1 illustrates an example surgical console, in accordance with certain embodiments of the present disclosure.

FIG. 1 illustrates an example of a surgical console 101, according to certain embodiments. Surgical console 101 may be configured to power one or more tools 103, which may include vitrectors, scissors, forceps, and injection or extraction modules. Other tools 103 may also be used. The surgical console 101 may include a display 109 for displaying information to a user (the display may also incorporate a touchscreen for receiving user input).

In operation, surgical console 101 may function to assist a surgeon in performing various ophthalmic surgical procedures, such as vitrectomy and similar procedures. In embodiments where tool 103 is a vitrector, surgical console 101 includes one or more modules or components to drive the vitrector for the purpose of cutting the vitreous. For example, in certain embodiments, surgical console 101 may include an actuation module coupled to one or more ports 107 of the surgical console 101 and having an actuator, such as an electromechanical motor or a pneumatic actuator, to drive the mechanical vitrector. In such embodiments, the vitrector may be operatively coupled to an actuator of the actuation module through one or more lines (e.g., fluid sealed tubes) 105 that connect to the port(s) 107. The actuation module drives a cutting motion of the vitrector, which cuts and removes the vitreous in a controlled fashion.

Note that line 105 may be representative of a number of tubes that may couple tool 103 with surgical console 101. For example, line 105 may be representative of a fluid line for powering tool 103 for cutting purposes, an optical fiber cable for conducting illumination light to the tool 103, as well as an aspiration or vacuum line for transporting the aspirated material back to surgical console 101.

Figure 2:
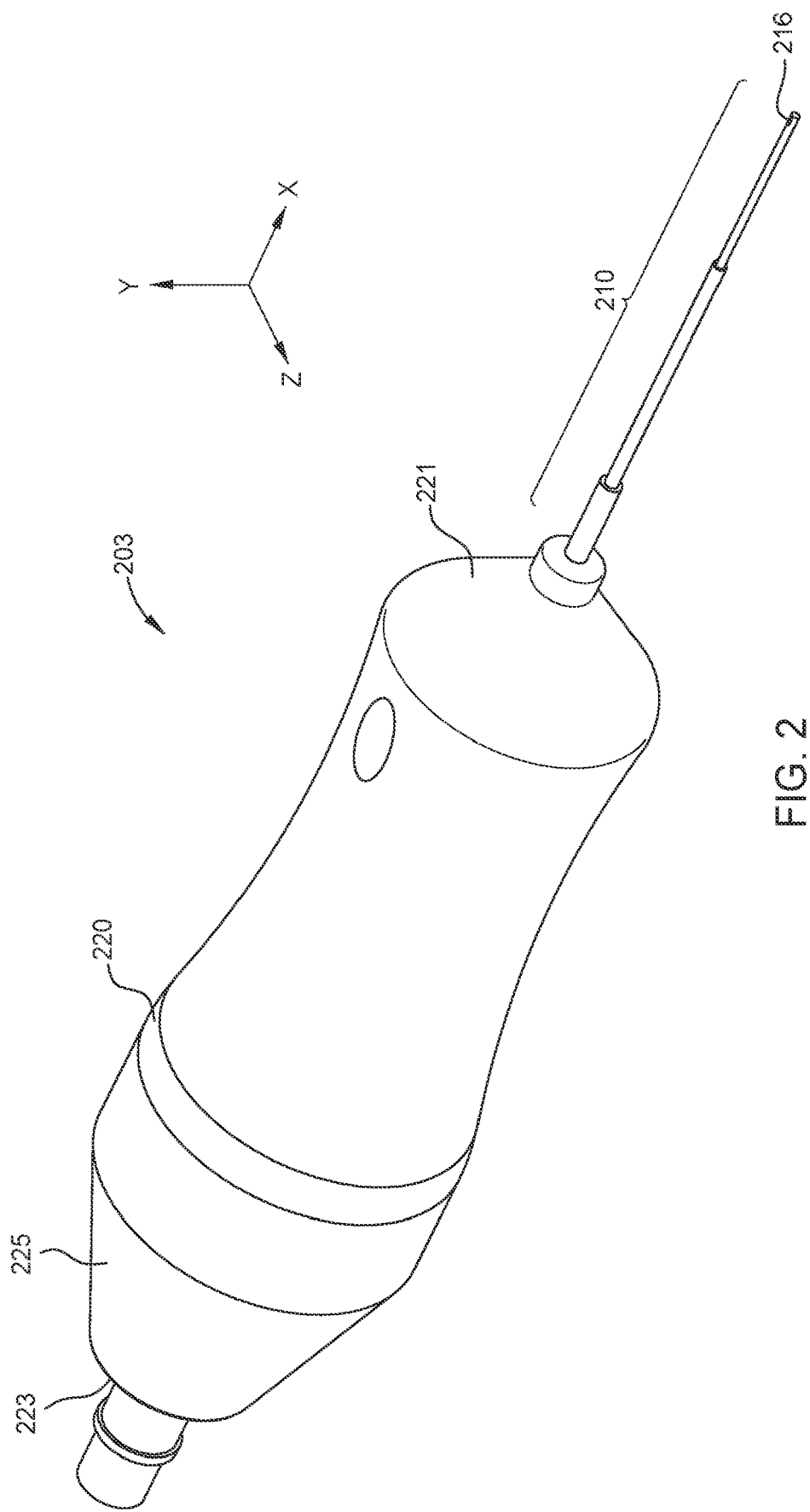
FIG. 2 illustrates an example vitrectomy probe, in accordance with certain embodiments of the present disclosure.
Figure 3:
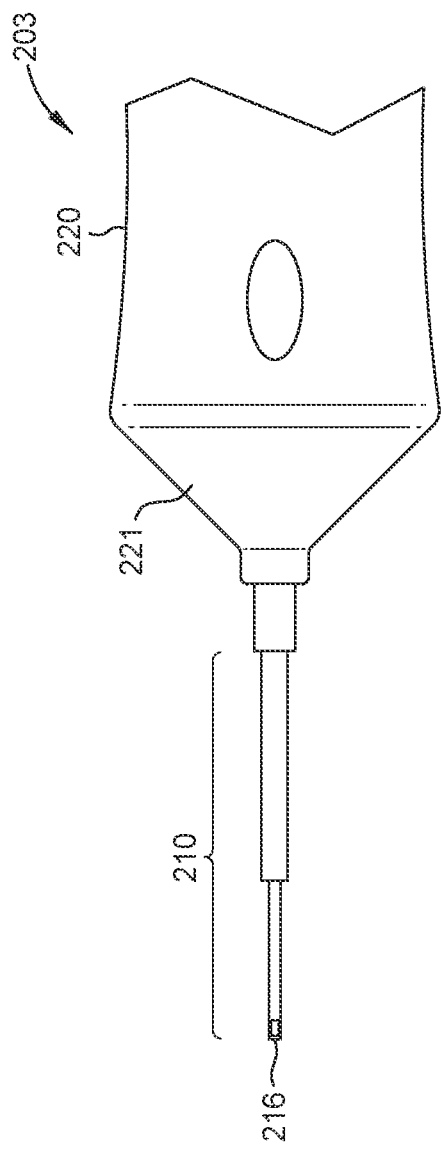
FIG. 3 illustrates a side vide of the vitrectomy probe of FIG. 2, in accordance with certain embodiments of the present disclosure.

FIGS. 2 and 3 illustrate a perspective view and a partial side view of an exemplary vitrector 203, respectively, according to certain embodiments described herein. FIGS. 2 and 3, therefore, are described together for clarity. Vitrector 203 is an example of tool 103. As depicted in FIGS. 2-3, vitrector 203 comprises a probe 210 and a base unit 220. Probe 210 is partially and longitudinally disposed through a distal end 221 of base unit 220 and may be directly or indirectly attached thereto within an interior chamber of base unit 220. Probe 210 may be inserted into an eye for performing vitrectomy. Note that, as described herein, a distal end or portion of a component refers to the end or the portion that is closer to a patient's body during use thereof. On the other hand, a proximal end or portion of the component refers to the end or the portion that is distanced further away from the patient's body.

Base unit 220 further provides a port 223 at a proximal end 225 thereof for one or more lines to be routed into an interior chamber of the base unit 220. In certain embodiments, port 223 may be representative of two or more ports. In certain embodiments, port 223 provides a portal for one or more fluid lines (e.g., line 105 of FIG. 1) coupled to an actuation module (e.g., in surgical console 101) for driving vitrector 203 for cutting purposes. In certain embodiments, port 223 may provide a portal for connection of the base unit 220 to a vacuum line that couples to a vacuum generator (e.g., in surgical console 101) for aspiration. In certain embodiments, port 223 may provide a portal for connection of the base unit 220 to an optical fiber cable that couples to one or more illumination light sources (e.g., in surgical console 101) for illumination. As further described in relation to FIG. 4, vitrector 203 comprises a cutting port 216 at the distal portion of probe 210. In certain embodiments, vitrector 203 is able to cut and aspirate the vitreous through this port 216.

Figure 4:
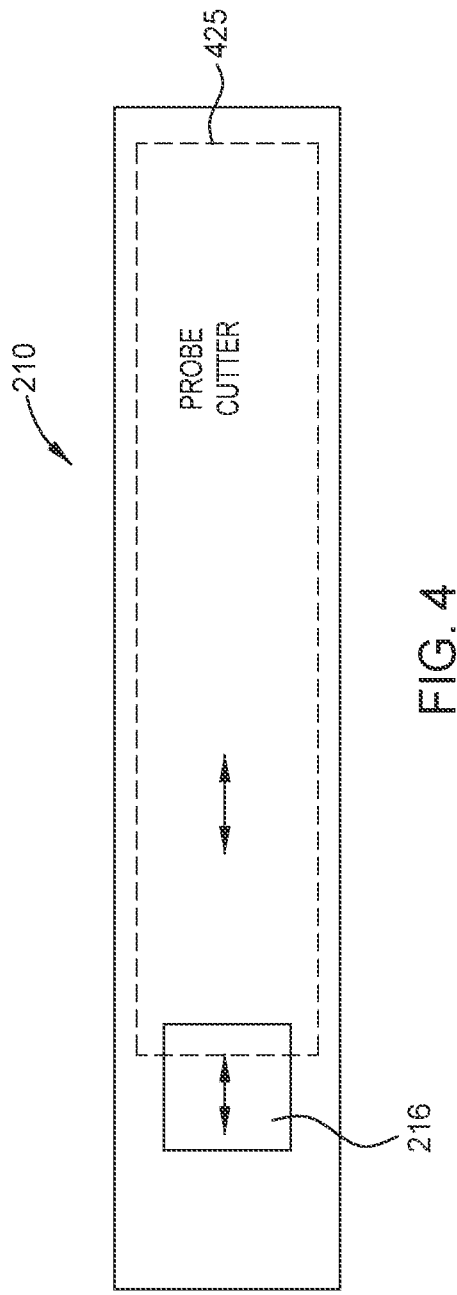
FIG. 4 illustrates an example cutting mechanism of the vitrectomy probe of FIG. 2, in accordance with certain embodiments of the present disclosure.

FIG. 4 illustrates an example of a cutting mechanism used in conjunction with vitrector 203 of FIGS. 2 and 3. More specifically, FIG. 4 illustrates the distal end of probe 210 of vitrector 203, the distal end probe 210 housing a probe cutter 425 that acts as a cutting device. Probe cutter 425 reciprocates inside probe 210. In certain embodiments, probe cutter 425 is a hollow tube with a sharpened tip. In certain embodiments, probe cutter 425 comprises a cutter port that is similar to and interacts with cutter port 216 of probe cutter 425 to increase the cutting efficiency and effectiveness. As the probe cutter 425 moves back and forth, the probe cutter 425 alternately opens and closes cutter port 216 with the sharpened tip of probe cutter 425. Each cycle of the probe cutter 425 through the distal end of probe 210 may cut through material such as vitreous in the cutter port 216 as the probe cutter 425 is closing. The surgically cut vitreous is then aspirated through probe 210. In certain embodiments, the surgically cut vitreous is aspirated from the circular area between the outer surface of probe cutter 425 and the inner surface of probe 210. In certain embodiments, the surgically cut vitreous is, in addition or instead, aspirated through probe cutter 425 (e.g., through the hollow compartment thereof).

Figure 5:
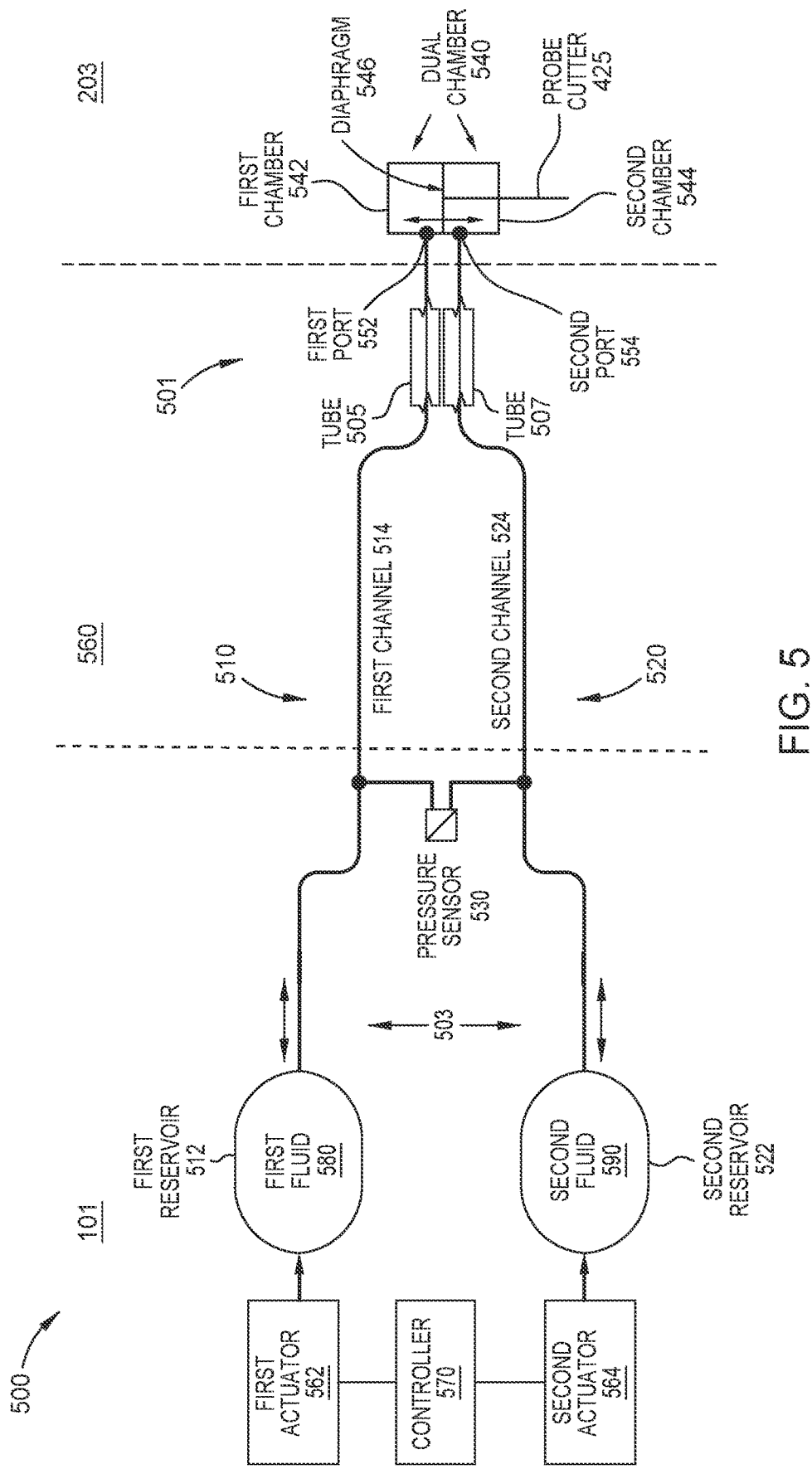
FIG. 5 illustrates a schematic of a system for an alternative fluid driven vitrectomy probe, in accordance with certain embodiments of the present disclosure.
Figure 6:
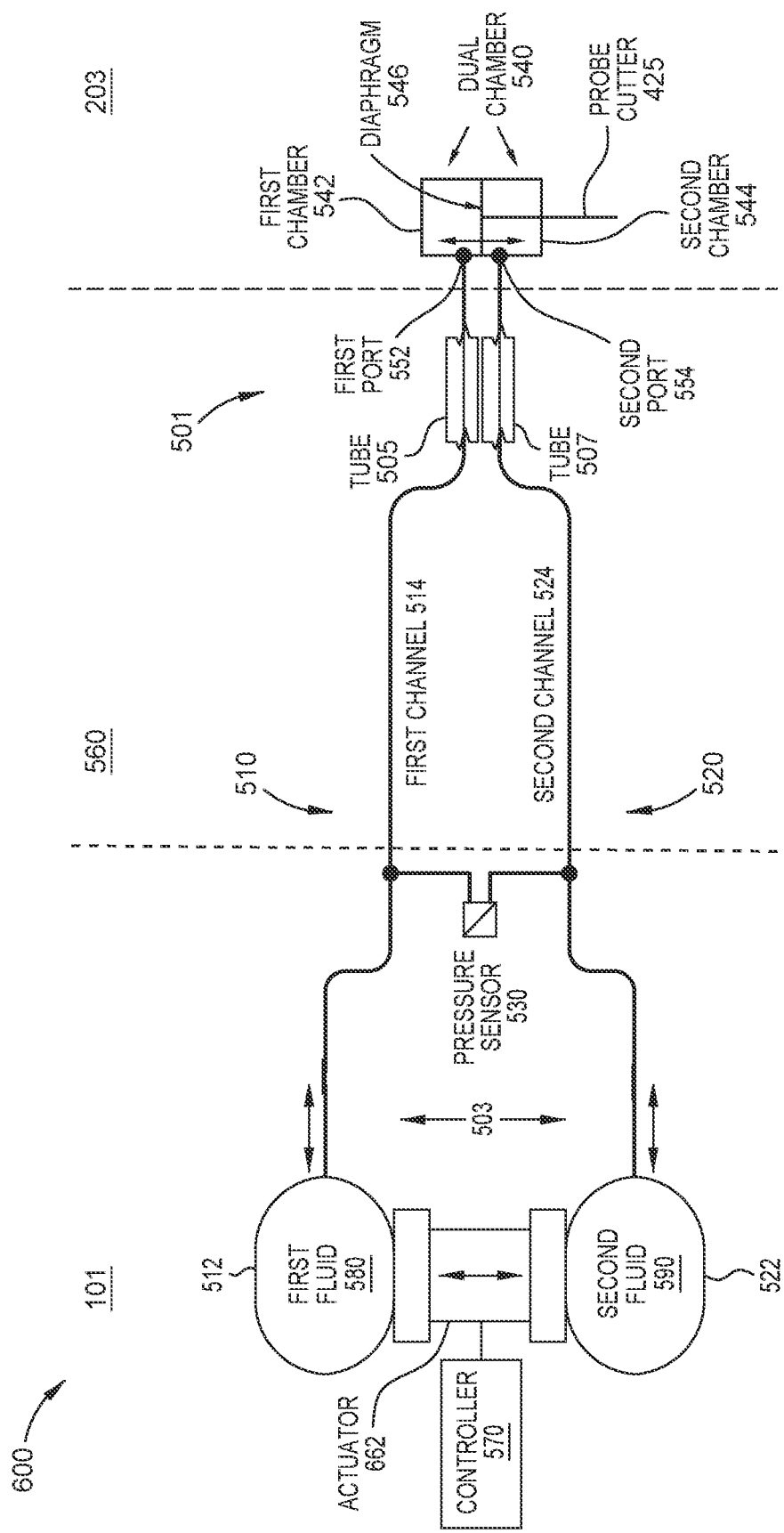
FIG. 6 illustrates a schematic of a system for an alternative fluid driven vitrectomy probe, in accordance with certain embodiments of the present disclosure.

FIGS. 5 and 6 illustrate schematic views of systems 500 and 600, respectively, for an alternative fluid driven vitrectomy probe, such as vitrector 203. Certain aspects of systems 500 and 600 are similar and thus, such aspects will be described with respect to FIGS. 5 and 6 together for clarity. Further, certain aspects that differ between systems 500 and 600 will be described separately. As shown, the systems 500, 600 include a first fluid pathway 510 and a second fluid pathway 520. The first fluid pathway 510 retains a first fluid 580 therein for driving a cutting motion of the vitrector 203 that is completely sealed from an environment external to the first and second fluid pathways 510, 520. The second fluid pathway 520 retains a second fluid 590 therein for driving a cutting motion of the vitrector 203 that is completely sealed from the environment external to the first and second fluid pathways 510, 520. In some embodiments, the fluid reservoir 580, first fluid pathway 510, tube 505, vitrector 203, tube 507, second fluid pathway 520, and second reservoir 522 may be completely sealed from the environment and installed/removed from the surgical system as a single unit. For example, when a user installs a new vitrector 203 for a surgical procedure, the user may install the first and second reservoir 512, 522 into the surgical console 101 and the attached tubes 505, 507 and vitrector 203 may extend from the surgical console 101 for use during the surgery. After the surgery, the first and second reservoirs 512, 522 along with the attached tubes 505, 507 and vitrector 203 may then be discarded or sterilized and re-used. In some embodiments, the pressure sensor 530 may also be a part of the reservoir to vitrector assembly or the pressure sensor 530 may be permanently resident in the surgical console 101 (and detect pressure, e.g., through physical contact with the fluid pathways or, for example, detect pressure using a non-contact method such as infrared pressure detection).

Because the fluid pathways are completely sealed, the first and second fluids may not be vented during reciprocation of the vitrector 203 (as found in conventional probes), but instead the first and second fluids may be retained in their respective first and second fluid pathways 510, 520 during the duration of the surgical procedure. In some embodiments, this may also result in less noise than a conventional vitrectomy system (which may generate noise as the fluids are vented through mufflers during the reciprocation of the vitrectomy probe). In certain embodiments, the first and second fluids 580, 590 and thus, the first and second fluid pathways 510, 520, are also sealed from each other. In certain other embodiments, the first and second fluids 580, 590 and thus, the first and second fluid pathways 510, 520, are exposed to each other.

The first fluid pathway 510 includes a first channel 514 coupling a first fluid reservoir 512 to a first chamber 542 of a dual chamber driver 540 disposed within the vitrector 203. Similarly, the second fluid pathway 520 includes a second channel 524 coupling a second fluid reservoir 522 to a second chamber 544 of the dual chamber driver 540. Accordingly, the first and second fluid reservoirs 512, 522 may be described as being located at proximal ends 503 of the channels 514, 524, whereas the dual chamber driver 540 is located at distal ends 501 thereof.

The dual chamber driver 540 is disposed within the vitrector 203 and includes the first chamber 542 and the second chamber 544. The chambers 542, 544 are separated from each other by a diaphragm 546 that is axially movable relative to the vitrector housing (e.g., base unit 220 of FIGS. 2-3) and between the chambers 542, 544. A probe cutter (e.g., probe cutter 425) is coupled to the diaphragm 546 and configured to move therewith. Movement of the diaphragm 546 and thus, the probe cutter 425, is driven by relative fluid pressures within the first and second chambers 542, 544.

As seen in FIGS. 5-6, each of the first and second channels 514, 524 is contained within a tube 505 and 507 (e.g., line(s) 105 of FIG. 1), respectively. However, in certain embodiments, a single tube for both channels may be also be used. Generally, the tubes 505, 507 are formed from a medical-grade and substantially fluid-impermeable material, including, without limitation, a plastic or polymer-based material. The tube 505 and thus, the first channel 514, directly couples to the first chamber 542 via a first port 552 of the first chamber 542 and, in certain aspects, proximally extends therefrom to an exterior 560 of the vitrector housing of vitrector 203. For example, the tube 505 may extend through port 223 of the base unit 220 of FIGS. 2-3. Similarly, the tube 507 and the second channel 524 directly couple to the second chamber 544 via a second port 554 of the second chamber 544 and, in certain aspects, proximally extend therefrom to the exterior 560 of the housing of vitrector 203 (e.g., through port 223 of base unit 220 of FIGS. 2-3).

The first and second fluid reservoirs 512, 522 are disposed at proximal ends 503 of the channels 514, 524 and, in certain aspects, are therefore external to the vitrector housing (e.g., base unit 220 of FIGS. 2-3). Each of the first and second fluid reservoirs 512, 522 includes a volume 516 or 526, respectively, that retains the first or second fluid 580, 590 and is actionable upon by an external actuator to drive the retained fluids in a distal or proximal flow direction within the fluid pathways 510, 520. Thus, the first and second fluid reservoirs 512, 522 may be inserted into one or more ports of a surgical console (e.g., ports 107 of surgical console 101 of FIG. 1) having one or more actuators therein that will act upon the reservoirs to alternately drive the retained fluids in the proximal or distal flow directions within each of the fluid pathways 510, 520. In certain embodiments, the first and second fluid reservoirs 512, 522 are balloons or flexible bags that may be alternately compressed by one or more actuators within surgical console 101 to alternate fluid flow direction within the fluid pathways 510, 520 (e.g., between the reservoirs 512, 522 and the dual chamber driver 540). Similar to the tubes 505, 507, the balloons or flexible bags may be formed from a medical-grade and substantially fluid-impermeable material, including, without limitation, a plastic or polymer-based material.

In the example depicted in FIG. 5, the surgical console 101 includes a first actuator 562 which acts upon the first reservoir 512, and a second actuator 564 which acts upon the reservoir 522. Thus, the fluid flow direction in each fluid pathway is driven by a separate actuator. However, in the example depicted in FIG. 6, the first and second reservoirs 512, 522 are acted upon by a single actuator 662. Thus, the fluid flow direction in both fluid pathways is driven by a single actuator. In certain embodiments, the one or more actuators are electromechanically-driven motors configured to act upon the first and second reservoirs 512, 522. In certain other embodiments, the one or more actuators are pneumatically-driven actuators driven by pressurized gas.

In certain embodiments, the systems 500, 600 further include one or more pressure sensors 530 and one or more system controllers 570. The pressure sensors 530 monitor pressure of the two fluid pathways 510, 520 in real time and the system controller 570 receives and processes the pressure data in real time. The system controller 570 may utilize the pressure information for controlling the actuators 562, 564, and 662 to drive fluid flow directions within the fluid pathways 510, 520.

In operation, first and second reservoirs 512, 522 are inserted into surgical console 101 via one or more ports 107. A controller 570 sends control signals to separate actuators 562, 564 (as shown in FIG. 5), or single actuator 662 (as shown in FIG. 6), to repetitively and alternately compress the first and second reservoirs 512, 522. The alternating compression of the reservoirs 512, 522 causes alternating fluid flow directions within the fluid pathways 510, 520, thus creating alternating fluid pressures within the first and second chambers 542, 544 of the dual chamber driver 540 and causing an oscillating cutting motion of the diaphragm 546 and probe cutter 425.

For example, in a first operation, the first reservoir 512 is compressed by the first actuator 562 or actuator 662, while the second actuator 564 or actuator 662 is simultaneously retracted from acting upon the second reservoir 522, thus creating a pressure differential between the fluid pathways 510, 520 and causing the first fluid 580 to flow towards the dual chamber driver 540 and the second fluid 590 to flow towards the second reservoir 522. As a result, the diaphragm 546 and probe cutter 425 are axially moved in a first direction from the first chamber 542 toward the second chamber 544. Subsequently, in a second operation, the second reservoir 522 is compressed by the second actuator 564 or actuator 662, while the first actuator 562 or actuator 662 is simultaneously retracted from acting upon the first reservoir 512, causing the second fluid 590 to flow towards the dual chamber driver 540 and the first fluid 580 to flow towards the first reservoir 512. As a result, the diaphragm 546 and probe cutter 425 are axially moved in a second direction from the second chamber 544 towards the first chamber 542.

The performance of the first and second operations may be considered a single cutting cycle of the vitrector 203. Generally, for the benefit of reducing traction (which can cause retinal detachment) during a vitrectomy procedure, the vitrector is desired to be operated at a faster cycle rate. The common understanding is the faster the better. As described above, the cycle rate of conventional air-driven vitrectors is limited by the speed at which air pressure can be adjusted. However, because the fluid pathways 510, 520 of the systems 500, 600 are completely sealed from the external environment, the systems 500, 600 may utilize an alternative fluid that can transmit pressure waves faster than air to drive the vitrector 203. Thus, the relative pressures within the fluid pathways 510, 520 can be adjusted at a faster rate as compared to air-driven vitrectors, resulting in a faster cutting cycle or speed of vitrector 203 and reduced traction. In certain embodiments, the first and second fluids 580, 590 are gases which can transmit pressure waves faster than air, such as hydrogen, helium, neon, or the like. In certain embodiments, the first and second fluids 580, 590 are liquids which can transmit pressure waves faster than air, such as water or saline.

As described above, a vitrector includes a first fluid pathway containing a first fluid and a second fluid pathway containing a second fluid that are completely sealed from an external environment. The fluid pathways are partially disposed within tubes that extend proximally and, in certain aspects, externally from a housing of the vitrector and are configured to be inserted or attached to a surgical console to drive flow directions of the first and second fluids contained therein. Alternating flow directions of the fluids within the fluid pathways drives an oscillating cutting motion of the vitrector. Because the fluid pathways are completely sealed from an external environment, an alternative fluid that can transmit pressure waves faster than air may be utilized as the first and second fluids, thus facilitating faster cutting rates than conventional air-driven vitrectomy probes and reducing traction of the vitrector.

EXAMPLE EMBODIMENTS

Embodiment 1: A surgical system, comprising: a surgical tool, comprising: a housing; a first fluid pathway retaining a first fluid and completely sealed from an external environment, the first fluid pathway comprising: a first chamber disposed within the housing and having a first port; and a first channel coupled to the first port and extending from the housing; a second fluid pathway retaining a second fluid and completely sealed from an external environment, the second fluid pathway comprising: a second chamber disposed within the housing and having a second port; and a second channel coupled to the second port and extending from the housing; a diaphragm disposed within the housing and separating the first chamber from the second chamber, the diaphragm axially movable relative to the housing and between the first chamber and the second chamber, wherein alternating a flow direction of the first and second fluids through the first and second fluid pathways axially drives the diaphragm in an oscillating manner; and a cutting member coupled to the diaphragm, wherein axial motion of the diaphragm causes axial motion of the cutting member; a controller producing an output signal representing a desired oscillation frequency of the cutting member; and a first actuator in communication with the controller and at least one of the first and second fluid pathways, the first actuator configured to receive the output signal of the controller and drive the flow direction of at least one of the first and second fluids in the first and second fluid pathways.

Embodiment 2: The surgical system of Embodiment 1 described above, wherein the first actuator is configured to drive the flow direction of both the first and second fluids.

Embodiment 3: The surgical system of Embodiment 1 described above, further comprising a second actuator, wherein the first actuator is configured to drive the flow direction of the first fluid and the second actuator is configured to drive the flow direction of the second fluid.

Embodiment 4: The surgical system of Embodiment 3 described above, wherein the first and second reservoirs are compressible balloons.

Embodiment 5: The surgical system of Embodiment 1 described above, wherein the first and second fluid pathways are completely sealed from an external environment.

Embodiment 6: The surgical system of Embodiment 1 described above, wherein the first actuator is electromechanically driven.

Embodiment 7: The surgical system of Embodiment 1 described above, wherein the first actuator is pneumatically driven.

The above-disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

What is claimed is:

1. A surgical system, comprising:
a surgical tool, comprising:
a housing;
a first fluid pathway retaining a first fluid and completely sealed from an external environment, the first fluid pathway comprising:
a first chamber disposed within the housing and having a first port;
a first channel coupled to the first port and extending from the housing; and
a first reservoir coupled to the first channel at an end opposite the first chamber, wherein the first reservoir comprises a first compressible balloon;
a second fluid pathway retaining a second fluid and completely sealed from the external environment, the second fluid pathway comprising:
a second chamber disposed within the housing and having a second port;
a second channel coupled to the second port and extending from the housing; and
a second reservoir coupled to the second channel at an end opposite the second chamber, wherein the second reservoir comprises a second compressible balloon;
a diaphragm disposed within the housing and separating the first chamber from the second chamber, the diaphragm axially movable relative to the housing and between the first chamber and the second chamber, wherein alternating a flow direction of the first and second fluids through the first and second fluid pathways axially drives the diaphragm in an oscillating manner;
a cutting member coupled to the diaphragm, wherein axial motion of the diaphragm causes axial motion of the cutting member; and
at least one actuator in communication with the first and second reservoirs, the at least one actuator configured to alternate the flow direction of the first and second fluids through the first and second fluid pathways by alternately compressing the first and second reservoirs.

2. The surgical system of claim 1, wherein the first and second fluids are gases.

3. The surgical system of claim 1, wherein the first and second fluids are liquids.

4. The surgical system of claim 1, wherein the first and second fluids comprise hydrogen, helium, or neon.

5. The surgical system of claim 1, wherein the first and second reservoirs are configured to be inserted into a surgical console for coupling to the at least one actuator.

6. The surgical system of claim 1, wherein the first and second fluid pathways are completely sealed from each other.

7. A surgical system, comprising:
a surgical tool, comprising:
a housing;
a first fluid pathway retaining a first fluid and completely sealed from an external environment, the first fluid pathway comprising:
a first chamber disposed within the housing and having a first port;
a first channel coupled to the first port and extending from the housing; and
a first reservoir coupled to the first channel at an end opposite the first chamber, wherein the first reservoir comprises a first compressible balloon;
a second fluid pathway retaining a second fluid and completely sealed from an external environment, the second fluid pathway comprising:
a second chamber disposed within the housing and having a second port;
a second channel coupled to the second port and extending from the housing; and
a second reservoir coupled to the second channel at an end opposite the second chamber, wherein the second reservoir comprises a second compressible balloon;
a diaphragm disposed within the housing and separating the first chamber from the second chamber, the diaphragm axially movable relative to the housing and between the first chamber and the second chamber, wherein alternating a flow direction of the first and second fluids through the first and second fluid pathways axially drives the diaphragm in an oscillating manner; and
a cutting member coupled to the diaphragm, wherein axial motion of the diaphragm causes axial motion of the cutting member;
a controller producing an output signal representing a desired oscillation frequency of the cutting member; and
at least one actuator in communication with the controller and the first and second reservoirs, the at least one actuator configured to receive the output signal of the controller and alternate the flow direction of the first and second fluids through the first and second fluid pathways by alternately compressing the first and second reservoirs.

8. The surgical system of claim 7, wherein the first and second fluids are gases.

9. The surgical system of claim 7, wherein the first and second fluids are liquids.

10. The surgical system of claim 7, wherein the first and second fluids comprise, hydrogen, helium, or neon.

11. The surgical system of claim 7, wherein the controller and the at least one actuator are disposed within a surgical console.

12. A surgical system, comprising:
a surgical tool, comprising:
a housing;
a first fluid pathway retaining a first fluid and completely sealed from an external environment, the first fluid pathway comprising:
a first chamber disposed within the housing and having a first port;
a first channel coupled to the first port and extending from the housing; and
a first compressible balloon coupled to the first channel at an end opposite the first chamber;
a second fluid pathway retaining a second fluid and completely sealed from the external environment, the second fluid pathway comprising:

a second chamber disposed within the housing and having a second port;

a second channel coupled to the second port and extending from the housing; and a second compressible balloon coupled to the second channel at an end opposite the second chamber;

a diaphragm disposed within the housing and separating the first chamber from the second chamber, the diaphragm axially movable relative to the housing and between the first chamber and the second chamber, wherein alternating a flow direction of the first and second fluids through the first and second fluid pathways axially drives the diaphragm in an oscillating manner; and a cutting member coupled to the diaphragm, wherein axial motion of the diaphragm causes axial motion of the cutting member;

a controller producing an output signal representing a desired oscillation frequency of the cutting member;

a first actuator in communication with the controller and the first compressible balloon, the first actuator configured to receive the output signal of the controller and drive the flow direction of the first fluid through the first fluid pathway; and a second actuator in communication with the controller and the second compressible balloon, the second actuator configured to receive the output signal of the controller and drive the flow direction of the second fluid through the second fluid pathway.

13. The surgical system of claim 12, wherein the first and second fluids are gases.

14. The surgical system of claim 12, wherein the first and second actuators are configured to alternately compress the first and second compressible balloons to supply alternating fluid flow directions within the first and second fluid pathways and create alternating fluid pressures within the first and second chambers.

15. The surgical system of claim 12, wherein the first and second fluids comprise hydrogen, helium, or neon.

16. The surgical system of claim 12, wherein the first and second fluid pathways are completely sealed from each other.

* * * * *